United States Patent [19]

Maier et al.

[11] Patent Number: 5,972,842
[45] Date of Patent: *Oct. 26, 1999

[54] HERBICIDAL CYANOPYRIDINES

[75] Inventors: Thomas Maier, Grunewaldstrasse; Stefan Scheiblich, Backhaushohol; Helmut Siegfried Baltruschat, Deyertstrasse, all of Germany

[73] Assignee: American Cyanamid Company, Madison, N.J.

[ * ] Notice: This patent is subject to a terminal disclaimer.

[21] Appl. No.: 08/900,222

[22] Filed: Jul. 24, 1997

Related U.S. Application Data

[60] Provisional application No. 60/033,052, Dec. 12, 1996.
[51] Int. Cl.⁶ .................................................. C07D 401/12
[52] U.S. Cl. ........................... 504/253; 504/250; 504/254; 504/244; 506/261; 506/276.1; 506/280.4; 506/288
[58] Field of Search ................. 546/261, 276.1, 546/280.4, 288; 504/250, 253, 254, 244

[56] References Cited

U.S. PATENT DOCUMENTS 5,824,624  10/1998  Kleeman et al. ...................... 504/242

FOREIGN PATENT DOCUMENTS 723960   7/1996  European Pat. Off. .
WO96/06096  2/1996  WIPO .

*Primary Examiner*—Jane Fan
*Attorney, Agent, or Firm*—Gregory M. Hill

[57] ABSTRACT

The novel cyanopyridines of the general formula (I)

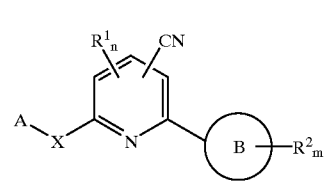

(A, B, $R^1$, $R^2$, X, m and n are defined in the specification) show selective herbicidal activity. The new compounds can be prepared according to known methods and can be used as herbicides in agriculture and related fields.

10 Claims, No Drawings

HERBICIDAL CYANOPYRIDINES

This application claims benefit of Provisional Application Ser. No. 60/033,052 filed Dec. 12, 1996.

BACKGROUND OF THE INVENTION

Pyridines, pyrimidines and their derivatives have many uses in the pharmaceutical area as well as in agriculture (herbicides, fungicides, acaricides, anthelmintics, bird repellents), as reagents, intermediates and chemicals for the polymer and textile industry.

The European patent application EP 0 692 474 discloses 2,5-diphenyloxy-4-cyanopyridines. Certain herbicidal 2-thienylmethoxypyridines are known from and EP 0 693 490 A.

The broad generic formula of the International patent application WO 96/06096 embraces 2-azolyl-5-aryloxy-cyanopyridines.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

The present invention provides novel 2,6-substituted cyanopyridines of formula I:

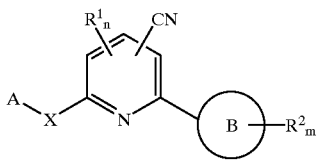

(I)

wherein
- A represents an optionally substituted aryl group or an optionally substituted 5- or 6-membered nitrogen-containing heteroaromatic group or a difluorobenzodioxolyl group;
- B represents a phenyl or thienyl group;
- m represents an integer from 0 to 5;
- n represents an integer from 0 to 2;
- $R^1$ (or each $R^1$) independently represents a hydrogen atom or an halogen atom,
- $R^2$ (or each $R^2$) independently represents a hydrogen atom, a halogen atom, an optionally substituted alkyl, alkenyl, alkinyl, alkoxy, alkoxyalkyl, alkoxyalkoxy, alkylthio, alkylsulphinyl, alkylsulphonyl group or a nitro, cyano, haloalkyl, haloalkoxy, haloalkylthio or $SF_5$ group, and
- X represents an oxygen or sulphur atom.

The new compounds show an excellent selective herbicidal activity in certain crops, such as maize and rice, and enhanced soil degradation.

It is another object of the invention to provide methods for controlling undesired plant growth by contacting said plants with a herbicidally effective amount of the new compounds.

It is another object of the invention to provide selective herbicidal compositions containing the new compounds as active ingredients.

It is another object of the invention to provide new processes for the preparation of the new compounds.

Those and other objects and features of the invention will become more apparent from the detailed description set forth hereinbelow.

DETAILED DESCRIPTION OF THE INVENTION

Surprisingly, it has now been found that good herbicidal activity is present in novel 2,6-disubstituted cyanopyridines of formula I:

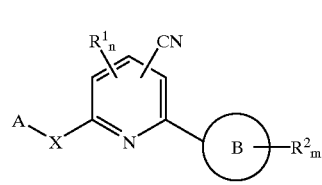

(I)

wherein
- A represents an optionally substituted aryl group or an optionally substituted 5- or 6-membered nitrogen-containing heteroaromatic group or a difluorobenzodioxolyl group;
- B represents a phenyl or thienyl group;
- m represents an integer from 0 to 5;
- n represents an integer from 0 to 2;
- $R^1$ (or each $R^1$) independently represents a hydrogen atom or an halogen atom,
- $R^2$ (or each $R^2$) independently represents a hydrogen atom, a halogen atom, an optionally substituted alkyl, alkenyl, alkinyl, alkoxy, alkoxyalkyl, alkoxyalkoxy, alkylthio, alkylsulphinyl, alkylsulphonyl group or a nitro, cyano, haloalkyl, haloalkoxy, haloalkylthio or $SF_5$ group, and
- X represents an oxygen or sulphur atom.

These compounds unexpectedly show considerable activity and high selectivity in certain crops, such as maize and rice, in pre- and post-emergence applications on both broadleaf and grassy weed species, and also show enhanced soil degradation.

An aryl group as substituent or part of other substituents or in the definition of A is suitably an optionally substituted phenyl group. Within the definition of A the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. As far as A is concerned the definition "aryl" does also include bicyclic systems which consist of a benzene ring fused with a 5- or 6-membered heterocyclic ring as defined above and in turn the 5- or 6-membered heterocycles may be fused with a benzene ring. Another preferred embodiment of A is a difluorobenzodioxolyl group of formula

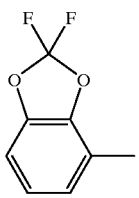

A preferably represents a phenyl, pyridyl or pyrazolyl group being substituted by one or more of the same or different substituents selected from halogen atoms, alkyl groups, alkoxy groups, cyano groups, haloalkyl groups, haloalkoxy groups alkylthio groups, haloalkylthio groups and $SF_5$ groups, in particular wherein A has a substituent in the meta-position relative to the point of attachment. Most preferred wherein A is meta-substituted by a chlorine atom, or a trifluoromethyl, trifluoromethoxy or difluoromethoxy group.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di- or trifluoroalkyl, -alkoxy and -alkylthio, especially trifluoromethyl, trifluoromethoxy, difluoromethoxy, difluoromethylthio, trifluoromethylthio or 2,2,2-trifluoroethoxy groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine aryd bromine atoms, and nitro, cyano, amino, hydroxyl, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio and halosulfanyl groups such as $SF_5$. 1 to 5 substituents may suitably be employed, 1 to 2 substituents being preferred.

Typically haloalkyl, haloalkoxy and haloalkylthio groups are trifluoromethyl, trifluoromethoxy, difluoromethoxy, trifluoroethoxy and trifluoromethylthio groups.

In formula I A preferably represents a group of formula a, b or c:

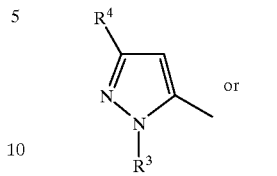

(a)

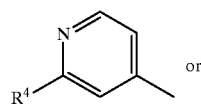

(b)

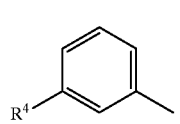

(c)

wherein $R^3$ is $C_{1-3}$ alkyl and $R^4$ is $C_{1-4}$ alkyl, $C_{1-3}$ haloalkyl, a halogen atom, cyano, $C_{1-3}$ haloalkoxy or $C_{1-3}$ haloalkylthio; while $R^1$ is hydrogen, fluorine, chlorine, $R^2$ is hydrogen, $C_{1-4}$ alkyl, hydrogen, chlorine, fluorine, trifluoromethyl, difluoromethoxy or trifluoromethoxy.

Preferred compounds of formula I are those wherein the cyano group is attached to the 4-position of the pyridine ring and/or wherein X is oxygen.

Particularly preferred are the compounds of formula IA and IB:

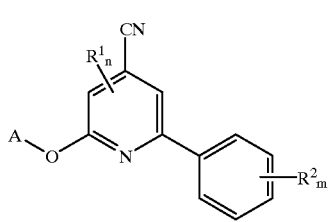

(IA)

wherein A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, $R^1$ and n have the meaning given above with n being preferably 0 or 2; $R^2$ each independently represent a hydrogen atom or a fluorine atom, one or two of them also a chlorine or bromine atom, or a trifluoromethyl, trifluormethoxy or a cyano group, one of them can further be a $C_1$–$C_4$-alkyl group, particularly tert-butyl, and m is 0 or an integer selected from 1 to 5;

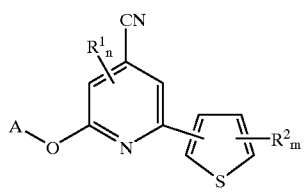

(IB)

wherein A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, $R^1$ and n have the meaning given above with n being preferably 0 or 2; $R^2$ each independently represent a hydrogen atom or a fluorine atom, one or two of them also a chlorine or bromine atom, or a trifluoromethyl, trifluormethoxy or a cyano group, one of them can further be a $C_1$–$C_4$-alkyl group, particularly tert-butyl, and m is 0 or an integer selected from 1 to 3.

The thienyl group may be attached in the 2- or 3-position with respect to the sulfur atom. 2-thienyl groups are preferred.

The compounds according to general formula I possess a high herbicidal activity within a wide concentration range and may be used in agriculture or related fields for the selective control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops, such as maize and rice.

The compounds according to the invention can be prepared by conventional methods, particularly as follows:

(A) A suitable process for the preparation of the compounds of general formula I comprises the reaction of a compound of formula III:

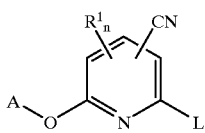

(III)

in which A, $R^1$ and n have the meaning given and L is a leaving group, with a compound of general formula IV,

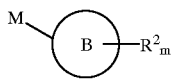

(IV)

in which B, $R^2$ and m have the meaning given, and

M represents a free or complexed metal selected from the group consisting of Li, Mg, Zn, B, Sn, in particular Li, MgCl, MgBr, ZnCl, ZnBr, or B(OH)$_2$ or trialkyl tin preferably under the conditions of a cross coupling reaction.

The cross coupling reaction is carried out as a rule in the presence of a transition metal complex, as for example described in J.Org.Chem.53 (1988) 4137, Tetrahedron 48 (1992) 8117, and Chem. Scr. 26 (1986) 305. Preferred transition metals Pd or N.

(B) Alternatively a compound of formula V:

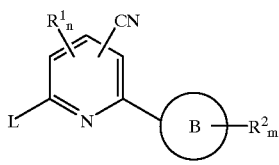

(V)

is reacted with a compound of general formula VI

A—XM$^1$ (VI)

wherein

A, B, $R^1$, $R^2$, m, n and X are defined as in claims 1 to 7;

L represents a suitable leaving group; and

M$^1$ represents a metal atom.

The reactions according to (A) and (B) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcohols, or water, or mixtures thereof. The reaction is carried out at a temperature between ambient temperature and the reflux temperature of the reaction mixture, preferably at elevated temperature, especially at reflux temperature.

The reactions may be carried out in the presence of a basic compound such as an alkali hydroxide, bicarbonate or carbonate, e. g. sodium or potassium hydroxide, bicarbonate or carbonate, a alkali alkoxide, e. g. sodium ethoxide, or an organic base such as triethylamine.

A hydroxy compound used in the above reactions may be present in form of a salt, preferably as a salt of an alkali metal, particularly of sodium or potassium. The presence of a copper salt may be suitable.

Suitable leaving groups L are e.g. alkyl- and arylsulfonyl, alkyl- and arylsulfonyloxy, perfluoroalkylsulfonyloxy, nitro and halogen, particularly fluorine, chlorine and bromine groups.

The compounds used as starting material are partly known and partly novel. The invention relates to the novel intermediates, in particular to the compounds of formulae III and V, which can be prepared analogously to known methods.

Intermediates of formula III and V can suitably be prepared from commercially available compounds of formula VII

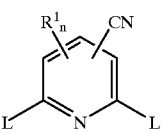

(VII)

in which each L represents a leaving group, by conventional methods known in pyridine chemistry, as described in: G. R. Newkome, "Pyridine and its Derivatives", in The Chemistry of Heterocyclic Compounds, Vol. 14, Part 5, Eds. A. Weissberger and E. C. Taylor, John Wiley & Sons, New York—Chichester—Brisbane—Toronto—Singapore 1984.

For the preparation of the intermediates of formula III the compound of formula VII is reacted with a compound of formula VI essentially under the same conditions given for method (B).

For the preparation of the intermediates of formula IV the compound of formula VII is reacted with a compound of formula IV essentially under the same conditions given for method (A).

The present invention also provides the use of the compounds of formula I as herbicides. Further, in accordance with the invention there is provided a method of combating undesired plant growth at a locus by treating the locus with a composition according to the invention or an effective amount of a compound of formula I. As a useful action is by foliar spray application, the locus is most suitably the plants in a crop area, typical crops being cereals, maize, soya bean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The present invention also extends to a method of making a herbicidal composition of the invention which comprises blending a compound of formula I with at least one carrier.

Preferably there are at least two carriers in a composition of the present invention, at least one of which is a surface-active agent.

A carrier in a composition according to the invention is any material with which the active ingredient is formulated to facilitate application to the locus to be treated, which may be, as appropriate, a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; amides, for example DMF, aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which: is a surface-active agent facilitates this process of dilution. Thus preferably at least one carrier in a composition according to the invention is a surface active agent. For example, the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythrol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or earth alkali metal salts, preferably sodium salts, or sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other active ingredients, for example, compounds possessing insecticidal or fungicidal properties, or other herbicides.

A formulation containing a compound according to the invention can consist of 100 g of active ingredient (compound of formula 1), 30 g of disperging agent, 3 g of antifoaming agent, 2 g of structure agent, 50 g of anti-freezing agent, 0.5 g of a biocidal agent and water ad 1000 ml. Prior to use it is diluted with water to give the desired concentration of active ingredient.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

PREPARATION OF COMPOUNDS OF FORMULA I

EXAMPLE 1

2-Chloro-4-cyano-6-(1'-methyl-3'-trifluoromethylpyrazol-5'-yloxy)pyridine

A mixture of 4-cyano-2,6-dichloropyridine (1.7 g, 10 mmol), and potassium carbonate (1.4 g, 10 mmol) in anhydrous acetonitrile (50 ml) is heated to 50° C. and 5-hydroxy-1-methyl-3-trifluoromethylpyrazole (1.7 g, 10 mmol) is added during a period of 3 hours. After further 30 min at 50° C. the reaction mixture is cooled to ambient temperature, deluted with pentane/ethyl acetate (volume ratio of 1/1) and filtered through a bed of silica gel. The solvents are removed and the residue is washed with pentane. Colorless crystals (1.6 g, 53% yield) of melting point 163° C. are obtained.

4-Cyano-2-(1'-methyl-3'-trifluoromethylpyrazol-5'-yloxy)-6-(4"-trifluoromethylphenyl)pyridine A mixture of bis(benzonitrile)palladium(II)chloride (0.57 g, 1.5 mmol) and 1,4-bis(diphenylphosphino)butane (0.63 g, 1.5 mmol) in anhydrous toluene (30 ml) is heated to reflux under a atmosphere of nitrogen. After 2 hours 4-trifluoromethylbenzeneboronic acid (1 g, 5.3 mmol), 2-chloro4-cyano-6-(1-methyl-3-trifluoromethylpyrazol-5-yloxy)pyridine (1.6 g, 5.2 mmol), ethanol (7.5 ml) and a 1 M hydrous solution of sodium carbonate (15 ml) is added and the mixture is heated to reflux for additional 3 days under a nitrogen atmosphere. The reaction mixture is deluted with pentane/ethyl acetate (volume ratio of 1/1) and filtered through a bed of silica gel. The filtrate is washed with water, dried over anhydrous magnesium sulfate and the solvents are removed in vacuo. The residue is purified by flash silica gel chromatography using pentanelethyl acetate (volume ratio 8/2). Colorless crystals (0.4 g, 18% yield) of melting point 144° C. are obtained.

The compounds of the examples 2 to 40 are obtained analogously:

| Example | Compound |
|---|---|
| 2 | 6-(4'-chlorophenyl)-4-cyano-2-(1"-methyl-3"-trifluoromethylpyrazol-5'-yloxy)pyridine; m.p.: 177–178° C. |
| 3 | 4-cyano-2-(1'-methyl-3'-trifluoromethylpyrazol-5'-yloxy)-6-(4"-fluoro-3"-chlorophenyl)pyridine |
| 4 | 4-cyano-2-(3'-trifluoromethylphenoxy)-6-(4"-trifluoromethylphenyl)pyridine; m.p.: 81–82° C. |

-continued

| Example | Compound |
|---|---|
| 5 | 6-(4'-chlorophenyl)-4-cyano-2-(3"-trifluoromethyl-phenoxy)pyridine; m.p.: 89–90° C. |
| 6 | 4-cyano-2-(2'-chloropyrid-4'-yloxy)-6-(4"-trifluoromethylphenyl)pyridine |
| 7 | 4-cyano-2-(2'-trifluoromethylpyrid-4'-yloxy)-6-(4"-trifluoromethylphenyl)pyridine |
| 8 | 4-cyano-2-(2'-difluoromethoxypyrid-4'-yloxy)-6-(4"-trifluoromethylphenyl)pyridine |
| 9 | 4-cyano-2-(1'-methyl-3'-trifluoromethylpyrazol-5'-yloxy)-6-(5"-chlorothien-2"-yl)pyridine |
| 10 | 4-cyano-2-(2'-chloropyrid-4'-yloxy)-6-(3"-trifluoromethylphenyl)pyridine, |
| 11 | 4-cyano-2-(1'-methyl-3'-trifluoromethylpyrazol-5'-yloxy)-6-(5"-trifluoromethylthien-2"-yl)pyridine |
| 12 | 4-cyano-2-(1'-methyl-3'-trifluoromethylpyrazol-5'-yloxy)-6-(4"-fluorophenyl)pyridine |
| 13 | 4-Cyano-3,6-difluoro-2-(1'-methyl-3'-trifluoromethyl-pyrazol-5'-yloxy)-6-(4"-trifluoro-methylphenyl)pyridine |
| 14 | 4-cyano-2-(2'-cyanopyrid-4'-yloxy)-6-(4"-trifluoromethylphenyl)pyridine |
| 15 | 4-cyano-2-(1'-methyl-3'-cyanopyrazol-5'-yloxy)-6-(4"-trifluoromethylphenyl)pyridine |
| 16 | 4-cyano-2-(3'-difluoromethoxyphenoxy)-6-(4"-trifluoromethylphenyl)pyridine |
| 17 | 4-cyano-2-(3'-trifluoromethoxyphenoxy)-6-(4"-trifluoromethylphenyl)pyridine |
| 18 | 4-cyano-2-(3'-cyanophenoxy)-6-(4"-trifluoromethylphenyl)pyridine |
| 19 | 4-cyano-2-(1'-methyl-3'-isopropylpyrazol-5'-yloxy)-6-(4"-trifluoromethylphenyl)pyridine |
| 20 | 4-cyano-2-(1'-methyl-3'-difluoromethoxypyrazol-5'-yloxy)-6-(4"-trifluoromethylphenyl)pyridine |
| 21 | 4-cyano-2-(2'-(2",2",2"-trifluoroethoxy)pyrid-4'-yloxy)-6-(4"'-trifluoromethylphenyl)pyridine |
| 22 | 4-cyano-2-(2'-difluoromethylthiopyrid-4'-yloxy)-6-(4"-trifluoromethylphenyl)pyridine |
| 23 | 4-cyano-2-(3'-difluoromethylthiophenoxy)-6-(4"-trifluoromethylphenyl)pyridine |
| 24 | 4-cyano-6-(4'-trifluoromethylphenyl)-2-(3"-trifluoromethyl-thiophenoxy)pyridine |
| 25 | 4-cyano-6-(4'-tert-butyl-phenyl)-2-(3"-trifluoromethyl-phenoxy)pyridine |
| 26 | 4-cyano-2-(1'-ethyl-3'-trifluoromethylpyrazol-5'-yloxy)-6-(4"-trifluoromethylphenyl)pyridine |
| 27 | 4-cyano-6-(4'-isopropylphenyl)-2-(3"-trifluoromethyl-phenoxy)pyridine |
| 28 | 6-(4'-bromophenyl)-4-cyano-2-(3"-trifluoromethyl-phenoxy)pyridine |
| 29 | 4-cyano-2-(1'-methyl-3'-trifluoromethyl-4'-fluoro-pyrazol-5'-yloxy)-6-(4"-trifluoromethylphenyl)pyridine |
| 30 | 4-cyano-2-(1'-methyl-3'-trifluoromethyl-4'-chloro-pyrazol-5'-yloxy)-6-(4"-trifluoromethylphenyl)pyridine |
| 31 | 6-(4'-chlorophenyl)-4-cyano-2-(3'-trifluoromethyl-phenoxy)pyridine |
| 32 | 4-cyano-2-(1'-methyl-3'-trifluoromethylpyrazol-5'-yloxy)-6-(4"-trifluoromethoxyphenyl)pyridine |
| 33 | 4-cyano-2-(1'-methyl-3'-trifluoromethylpyrazol-5'-yloxy)-6-(4"-trifluoromethylthiophenyl)pyridine |
| 34 | 6-(4'-difluoromethylthiophenyl)-4-cyano-2-(1"-methyl-3"-trifluoromethylpyrazol-5"-yloxy)pyridine |
| 35 | 4-cyano-6-(4'-ethylphenyl)-2-(1"-methyl-3"-trifluoro-methylpyrazol-5"-yloxy)pyridine |
| 36 | 6-(4'-chlorophenyl)-4-cyano-3,5-difluoro-2-(1"-methyl-3"-trifluoromethylpyrazol-5"-yloxy)pyridine |
| 37 | 6-(3',4'-difluorophenyl)-4-cyano-2-(1"-methyl-3"-trifluoromethylpyrazol-5"-yloxy)pyridine |
| 38 | 6-(2',4'-difluorophenyl)-4-cyano-2-(1"-methyl-3"-trifluoromethylpyrazol-5"-yloxy)pyridine |
| 39 | 4-cyano-3,5-difluoro-2-(3'-trifluoromethylphenoxy)-6-(4"-trifluoromethylphenyl)pyridine |
| 40 | 4-cyano-2-(3'-trifluoromethylphenoxy)-6-(3"-trifluoromethylphenyl)pyridine; m.p.: 78–79° C. |

PRE-EMERGENCE HERBICIDAL EVALUATION OF TEST COMPOUNDS

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting the pots are sprayed with the selected aqueous acetone solution containing test compound in sufficient quantity to rating provide the equivalent of about 0.025 to 0.4 kg per hectare of test compound per pot. The treated pots are then placed on greenhouse benches, watered and cared for in accordance with conventional greenhouse procedures. From 2 to 4 weeks after treatment, the tests are terminated and each pot is examined and rated according to the system set forth below.

| Rating System | % Difference in Growth — from the check |
|---|---|
| 0 — No effect | 0 |
| 1 — Trace effect | 1–5 |
| 2 — Slight effect | 6–15 |
| 3 — Moderate effect | 16–29 |
| 4 — Injury | 30–44 |
| 5 — Definite injury | 45–64 |
| 6 — Herbicidal effect | 65–79 |
| 7 — Good herbicidal effect | 80–90 |
| 8 — Aproaching complete kill | 91–99 |
| 9 — Complete kill | 100 |

| Plant Species Used | | |
|---|---|---|
| TRZAW | Triticum aestivum | winter wheat |
| HORVW | Hordeum vulgare | winter barley |
| ZEAMX | Zea mays | maize |
| ORYSA | Oryza sativum | rice |
| GLYMA | Glycine max | soyabeans |
| ALOMY | Alopecurus myosuroides | blackgrass |
| DIGSA | Digitaria sanguinalis | crabgrass |
| ECHCG | Echinochloa crus-galli | barnyardgrass |
| SETVI | Setaria viridis | green foxtail |
| ABUTH | Abutilon theophrasti | velvetleaf |
| AMBEL | Ambrosia artemisiifolia | ragweed |
| IPOHE | Ipomoea hederacea | morning glory |
| MATIN | Matricaria inodora | mayweed |
| STEME | Stellaria media | chickweed |
| CHEAL | Chenopodium album | lambsquarters |
| AMBEL | Ambrosia artemiisifolia | ragweed |
| CASOB | Cassia (Senna) obtusifolia | sicklepod |
| GALAP | Galium aparine | cleaver |
| LAMPU | Lamium purpureum | deadnettle |
| VERPE | Veronica persica | speedwell* |

*only post-emergence

The herbicidal performance of the active ingredients of the present invention is evident from the test results which are recorded in Table 1 below. The compound of the invention, i.e. Example 1, is selective in wheat, maize and rice up to 100 g/ha. At this dose important grasses such as Digitaia and Setara were well controlled. The same hold true for broad-leaved weed species such as Ambrosia, Cassia, Lamium, Matricada and Stellana.

TABLE 1

| dose kg/ha a.i. | Exa. No. | TRZAW | HORVW | ZEAMX | ORYSA | GLXMA | ALOMY | DIGSA | ECHCG | SETVI | ABUTH | AMBEL | CASOB | GALAP | IPOHE | LAMPU | MATIN | STEME |
|---|---|---|---|---|---|---|---|---|---|---|---|---|---|---|---|---|---|
| 0.4000 | 1 | 3 | 4 | 2 | 2 | 4 | 7 | 9 | 5 | 9 | 9 | 9 | 9 | 7 | 9 | 9 | 9 | 9 |
| 0.1000 | 1 | 2 | 4 | 1 | 1 | 3 | 3 | 8 | 3 | 8 | 7 | 8 | 8 | 5 | 7 | 9 | 9 | 9 |
| 0.0250 | 1 | 1 | 2 | 1 | 0 | 2 | 2 | 7 | 1 | 4 | 4 | 4 | 3 | 4 | 7 | 3 | 6 |
| 0.0125 | 1 | 0 | 2 | 0 | 0 | 1 | 1 | 3 | 0 | 3 | 2 | 4 | 1 | 2 | 3 | 6 | 6 | / |
| 0.0250 | 4 | 1 | 3 | 1 | 0 | 2 | 3 | / | 1 | 6 | 6 | / | 2 | 3 | 3 | 6 | 7 | 5 |
| 0.1000 | 5 | 1 | 2 | 2 | 1 | 1 | 2 | / | 1 | 5 | 3 | / | 2 | 1 | 2 | 4 | 7 | 2 |
| 0.4000 | 40 | 2 | 4 | 2 | 1 | 2 | 6 | / | 3 | 9 | 5 | / | 5 | 2 | 3 | 7 | 8 | 9 |

POST-EMERGENCE HERBICIDAL EVALUATION OF TEST COMPOUNDS

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels equivalent of about 0.025 to 0.4 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided below. A rating 0 indicates growth as untreated check, a rating 9 indicates death. The results of the test are set out in Table 2 below.

The compound of the invention, i.e. example 1 was sufficiently selective in rice up to 400 g/ha and in wheat up to 100 g/ha. At these doses good cross-spectrum control of grasses and broad-leaved weeds was recorded.

A represents a phenyl, pyridyl, or pyrazoyl group being substituted by one or more of the same or different substituents selected from halogen atoms, alkyl groups, alkoxy groups, cyano groups, haloalkyl groups, haloalkoxy groups. alkylthio groups, haloalkylthio groups and $SF_5$ groups or a difluorobenzodioxolyl group;

B represents a thienyl group;

m represents an integer from 0 to 5;

n represents an integer from 0 to 2;

$R^1$ (or each $R^1$) independently represents a hydrogen atom or an halogen atom, $R^2$ (or each $R^2$) independently represents a hydrogen atom, a halogen atom, an optionally substituted alkyl, alkenyl, alkinyl, alkoxy, alkoxyalkyl, alkoxyalkoxy, alkylthio, alkylsuphinyl, alkylsuphonyl group or a nitro, cyano, haloalkyl, haloalkoxy, haloalkylthio or $SF_5$ group in which the optional substituents are selected from the group consisting of phenyl, halogen atoms, nitro, cyano, hydroxyl, $C_1$–$C_4$alkoxy, $C_1$–$C_4$haloalkoxy and $C_1$–$C_4$alkoxycarbonyl groups, and X represents an oxygen or sulphur atom.

TABLE 2

| dose kg/ha a.i. | Exa. No. | TRZAW | HORVW | ZEAMX | ORYSA | GLXMA | ALOMY | DIGSA | SETVI | ABUTH | AMBEL | CASOB | GALAP | IPOHE | LAMPU | MATIN | STEME | VERPE |
|---|---|---|---|---|---|---|---|---|---|---|---|---|---|---|---|---|---|---|
| 0.4000 | 1 | 3 | 3 | 4 | 2 | 6 | 6 | 6 | 9 | 9 | 7 | 7 | 9 | 9 | 9 | 8 | 9 | 9 |
| 0.1000 | 1 | 2 | 3 | 3 | 1 | 5 | 4 | 5 | 7 | 7 | 7 | 7 | 6 | 9 | 9 | 8 | 9 | 9 |
| 0.0250 | 1 | 2 | 2 | 2 | 1 | 5 | 2 | 4 | 4 | 6 | 6 | 6 | 4 | 9 | 8 | 7 | 8 | 9 |
| 0.4000 | 4 | 3 | 4 | 5 | 5 | 6 | 7 | / | 8 | 7 | / | 7 | 8 | 9 | 8 | 6 | 6 | 9 |
| 0.1000 | 5 | 2 | 2 | 2 | 2 | 4 | 4 | / | 4 | 3 | / | 7 | 2 | 4 | 4 | 4 | 4 | 9 |
| 0.1000 | 40 | 2 | 2 | 2 | 2 | 5 | 4 | / | 6 | 4 | / | 7 | 5 | 6 | 6 | 5 | 4 | 9 |

We claim:

1. A compound of the general formula (I)

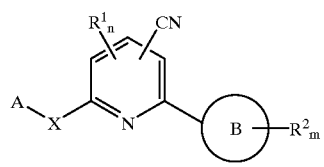

wherein

2. A compound as claimed in claim 1 wherein A represents a phenyl, pyridyl or pyrazolyl group being substituted by one or more of the same or different substituents selected from the group consisting of halogen atoms, alkyl groups, alkoxy groups, cyano groups, haloalkyl groups, haloalkoxy groups alkylthio groups, haloalkylthio groups and $SF_5$ groups.

3. A compound as claimed in claim 1 wherein A has a substituent in the meta-position relative to the point of attachment.

4. A compound as claimed in claim 3 wherein A is meta-substituted by a chlorine atom, or a trifluoromethyl, trifluoromethoxy or difluoromethoxy group.

5. A compound as claimed in claim 2 wherein the cyano group is attached to the 4-position of the pyridine ring.

6. A compound as claimed in claim 1 wherein X is oxygen.

7. A compound of formula I B

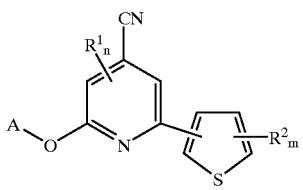

(IB)

wherein A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, $R^1$ and n have the meaning given above; $R^2$ each independently represent a hydrogen atom or a fluorine atom, one or two of them also a chlorine or bromine atom, or a trifluoromethyl, trifluormethoxy or a cyano group, one of them can further be a $C_1$–$C_4$-alkyl group, and m is 0 or an integer from 1 to 3.

8. A compound according to claim 1 selected from the group consisting of:

4-cyano-2-(1'-methyl-3'-trifluoromethylpyrazol-5'-yloxy)-6-(5"-chlorothien-2"-yl)pyridine, and 4-cyano-2-(1'-methyl-3'-trifluoromethylpyrazol-5'-yloxy)-6-(5"-trifluoromethylthien-2"-yl)pyridine.

9. A herbicidal composition which comprises at least one compound as claimed in claim 1 and a carrier and/or a surface-active agent.

10. A method of combating undesired plant growth at a locus, which comprises treating the locus with an effective amount of at least one compound as claimed in claim 1.

* * * * *